United States Patent
Suh et al.

(10) Patent No.: US 9,459,257 B2
(45) Date of Patent: Oct. 4, 2016

(54) HIGH-SPEED SCREENING APPARATUS FOR A RAMAN ANALYSIS-BASED HIGH-SPEED MULTIPLE DRUG

(75) Inventors: Yung Doug Suh, Daejeon (KR); Ki Seok Jeon, Daejeon (KR); Hyung Min Kim, Daejeon (KR); Kang Taek Lee, Daejeon (KR); Seung Min Jin, Chungcheongnam-do (KR); Sang Hwan Nam, Daejeon (KR); Yun Mi Bae, Chungcheongnam-do (KR); Haemi Lee, Daejeon (KR); Kyunghee Lee, Seoul (KR); Hyo Sun Park, Jeollanam-do (KR); Phil Hwan Kim, Daejeon (KR)

(73) Assignee: KOREA RESEARCH INSTITUTE OF CHEMICAL TECHNOLOGY, Daejeon-si (KR)

( * ) Notice: Subject to any disclaimer, the term of this patent is extended or adjusted under 35 U.S.C. 154(b) by 45 days.

(21) Appl. No.: 14/122,975
(22) PCT Filed: May 29, 2012
(86) PCT No.: PCT/KR2012/004223
§ 371 (c)(1),
(2), (4) Date: Nov. 27, 2013
(87) PCT Pub. No.: WO2012/165837
PCT Pub. Date: Dec. 6, 2012

(65) Prior Publication Data
US 2014/0113283 A1   Apr. 24, 2014

(30) Foreign Application Priority Data
May 29, 2011 (KR) .................. 10-2011-0050991
May 29, 2012 (KR) .................. 10-2012-0056775

(51) Int. Cl.
G01N 33/58 (2006.01)
G02B 21/36 (2006.01)
(Continued)

(52) U.S. Cl.
CPC .......... *G01N 33/587* (2013.01); *G01N 21/658* (2013.01); *G02B 21/367* (2013.01); *H04N 5/372* (2013.01)

(58) Field of Classification Search
CPC ..... G01N 21/65; G01N 21/658; H04N 5/372
See application file for complete search history.

(56) References Cited

U.S. PATENT DOCUMENTS 6,018,389 A * 1/2000 Kyle et al. ................ 356/301
6,643,012 B2  11/2003 Shen et al.
(Continued)

FOREIGN PATENT DOCUMENTS

JP    2007-147357 A    6/2007
JP    2008-241640 A    10/2008
(Continued)

OTHER PUBLICATIONS

"Oligonucleotide-Mediated Au—Ag Core-Shell Nanoparticles" Kahraman et al. Plasmonics (2009) 4:293-301.*
(Continued)

*Primary Examiner* — Kara E Geisel
*Assistant Examiner* — Dominic J Bologna
(74) *Attorney, Agent, or Firm* — Ladas & Parry LLP

(57) ABSTRACT

The present invention relates to a high-speed screening apparatus for a Raman analysis-based high-speed multiple drug. The screening apparatus according to the present invention may easily detect a Raman signal using a core-cap-shell nanoparticle which amplifies the Raman signal by $10^{12}$ times and has high reproducibility through Raman spectroscopy in which materials do not interfere with each other and a spectrum has a sharp peak to detect the Raman signal multiple times. Also, since a CCD camera, not a scanner, may be used as the detector, the screening apparatus may multiply screen the drug at a high speed without movement between molecules within a sample. In addition, since multicolors of 5 colors or more may be coated, the screening apparatus may be usefully used for screening various drugs.

12 Claims, 12 Drawing Sheets

(51) Int. Cl.
G01N 21/65 (2006.01)
H04N 5/372 (2011.01)

(56) References Cited

U.S. PATENT DOCUMENTS

| | | |
|---|---|---|
| 2003/0059820 A1 | 3/2003 | Vo-Dinh |
| 2003/0082516 A1* | 5/2003 | Straus ................. B82Y 20/00 435/4 |
| 2006/0054506 A1 | 3/2006 | Natan et al. |
| 2006/0105170 A1* | 5/2006 | Dobson et al. ............... 428/403 |
| 2006/0148104 A1* | 7/2006 | Marini et al. ................. 436/524 |
| 2008/0002198 A1 | 1/2008 | Sun et al. |
| 2008/0305489 A1 | 12/2008 | Thomas et al. |
| 2009/0140206 A1* | 6/2009 | Nie et al. ................. 252/301.16 |
| 2009/0323058 A1* | 12/2009 | Dyba ............................ 356/301 |
| 2010/0034743 A1* | 2/2010 | Cohen et al. ................... 424/9.1 |
| 2011/0124008 A1* | 5/2011 | Nam et al. ..................... 435/7.1 |

FOREIGN PATENT DOCUMENTS

| | | | |
|---|---|---|---|
| JP | 2009-222401 A | | 10/2009 |
| KR | 20100002742 A | * | 1/2010 |
| KR | 1020100002742 A | | 1/2010 |
| WO | 2005/062741 A2 | | 7/2005 |
| WO | 2008/116093 A2 | | 9/2008 |
| WO | 2008/122035 A1 | | 10/2008 |

OTHER PUBLICATIONS

Yunwei Charles Cao, et al; "Nanoparticles with Raman Spectroscopic Fingerprints for DNA and RNA Detection", Science, vol. 297, Aug. 30, 2002; pp. 1536-1538.

William E. Doering, et al; "Single-Molecule and Single-Nanoparticle SERS: Examining the Roles of Surface Active Sites and Chemical Enhancement", J. Phys. Chem. B; vol. 106, pp. 311-317; Published on Web Dec. 14, 2001.

Ying Fang, et al; "Measurement of the Distribution of Site Enhancements in Surface-Enhanced Raman Scattering", Science, vol. 321, Jul. 18, 2008; pp. 388-391.

Sarah J. Hurst, et al; "Maximizing DNA Loading on a Range of Gold Nanoparticle Sizes", Analytical Chemistry, vol. 78, No. 24, Dec. 15, 2006, pp. 8313-8318.

Katrin Kneipp et al; Single Molecule Detection Using Surface-Enhanced Raman Scattering (SERS); Physical Review Letters, vol. 78, No. 9, Mar. 3, 1997, pp. 1667-1670.

Shuming Nie et al; "Probing Single Molecules and Single Nanoparticles by Surface-Enhanced Raman Scattering", Science, vol. 275, Feb. 21, 1997, pp. 1102-1106.

W. Peter Wuelfing, et al; "Nanometer Gold Clusters Protected by Surface-Bound Monolayers of Thiolated Poly(ethylene glycol) Polymer Electrolyte", J. American Chemical Society, vol. 120, pp. 12696-12697, Published on Web Nov. 19, 1998.

* cited by examiner

HIGH-SPEED SCREENING APPARATUS FOR A RAMAN ANALYSIS-BASED HIGH-SPEED MULTIPLE DRUG

TECHNICAL FIELD

The present invention relates to a Raman analysis-based apparatus for screening multiple drugs at a high speed.

BACKGROUND ART

Drug development is an advanced country-type strategic process requiring a massive commitment of time and money of more than ten years and eight hundred million dollars, respectively. A well-developed social infrastructure is also necessary for drug development.

Broadly, the process of drug development can be divided into the discovery of a drug target by basic research, the selection of effective and lead materials by compound screening, the determination of a candidate drug, clinical research through pre-clinical work/clinical phase 1, and commercialization through clinical phases 2 and 3.

Of a total of 35,000 genes discovered thus far as drug targets, approximately 500 are currently under research for drug development, with a steady expansion of the development subject since the Human Genome Project. Once a drug target is selected, development of a screening method that is the most suitable and effective should be undertaken. The screening method can be divided into an in vitro assay and a cell-based assay. Major pharmaceutical companies possess libraries of compounds, typically amounting in number to ten of thousands to hundreds of millions, as screening targets, and such a number of compounds are employed from an early screening stage.

A great expense for this screening process has given rise to making every effort to design effective screening methods and develop high-speed and minimized apparatuses and reagents which allow the screening of as many compounds as possible within a short period of time.

A screening process for many compounds must be technically simple with high reproducibility. When a drug target is an enzyme, a relative easy approach is possible thanks to an abundant number of screening methods and reagents established therefor. However, because most of the biological processes taking place within cells are associated with interaction with proteins, a screening method based on interaction with proteins is the most effective among analysis methods for developing lead compounds. Great weight is given to such screening methods for the following reasons: a protein functions as it associates with another protein in vivo; a change in gene and protein expression, in intracellular location, and/or in structure through post-translational modification induces an altered interaction between proteins, resulting in a change in the activity and regulation of intracellular metabolisms and signaling pathways; and an abnormal protein interaction attributed to a genetic mutation directly leads to the onset of a disease. There are technologies for detecting protein interactions, including FRET (Fluorescence Resonance Energy Transfer), BRET (Bioluminescence Resonance Energy Transfer) and FP (Fluorescence Polarization), and a technical advance has also been achieved in apparatuses to which the technologies are applicable. In recent years, HCS (high-content screening) with automated high resolution microscopy has been introduced, whereby after cells are incubated with substances in multi-well plates, such as 96-well, 384-well plates, etc., phenomena associated with the quantitative change and transport of proteins within cells can be rapidly observed in a quantitative manner. HCS is now arising as the most interesting biological research method for world-leading pharmaceutical companies or research institutes because it allows the quantitative analysis of biological parameters, such as protein interaction, $Ca^{++}$ influx, etc., which are difficult to screen on a large scale with conventional methods, over the simple information obtained using conventional enzyme detection methods or reporter systems, for example, on enzyme activity, promoter strength, protein levels, etc.

Typically, a procedure for drug screening comprises preparation of compound aliquots, dilution, mixing of screening components, culturing and detection, analysis of screening data, and reporting on results. A high-throughput screening (hereinafter referred to as "HTS") system is used to rapidly process such a serial procedure. Advanced pharmaceutical companies are known to possess a compound library consisting of hundreds of millions of different compounds, and whenever a novel drug target is discovered, the companies take advantage of the HTS system in screening the compound library against the drug target. Thus, major pharmaceutical companies have accumulated tremendous data on biological activities of hundreds of millions of compounds, thus far. In order to more rapidly and effectively screen the compound library against thousands of drug targets, a curve-fitting tool capable of performing various functions including a QC function, error checking for overlapped data, calculation of relative activity (% activity), and extraction of biochemical parameters, such as $IC_{50}$, $K_i$, and $K_m$, is needed. In this regard, HTS which allows much data to be produced by one screening process is required. This new technology, aiming to overcoming problems associated with the conventional technology, is basically designed to evaluate synthetic compounds randomly on a mass scale through automation, and can reduce the time taken to determine candidate drugs as much as possible in association with automated synthesis of new materials (CCL), molecular design and systematic information management.

Prerequisites for HTS with a capacity of screening more than 10,000 different compounds a day are summarized as follows:

(1) Rapidity: Given a higher screening speed, an HTS can screen a higher number of compounds, and thus can complete its performance within a shorter time and at a lower expense.

(2) Expense: Reagents used in the screening process account for a large portion of the total screening expense. A measure must be taken toward financial retrenchment.

(3) Miniaturization: Miniaturization is not only one of the best measures to cut expenses for reagents, but can also reduce the time taken to perform a screening process. Besides, it can reduce laboratory space necessary for the instruments.

(4) Automation: Automation increases reproducibility of results as well as the speed of screening. Particularly, it makes a great contribution to the reduction of experimental error.

(5) Screening sensitivity: The sensitivity of a detection method is directly relevant to the quantity of samples to be used. High detection sensitivity is required because it takes a longer time to screen samples of lower sensitivity.

(6) Non-radioactive method: As high as 50% of the HTS methodologies developed thus far use radioactive substances. However, radioactive substances produce waste which must be specifically cared for, and thus are disadvantageous in terms of space, time and finances.

(7) Simplicity: Because a method operating with filtration, separation, washing, distinction, and solid-state extraction requires additional expense and processes, the screening process should be simplified in a liquid state as much as possible.

Pharmaceutical companies have made enormous investments in the development of chemical approaches to compounds, and HTS technology. As a result, the number of drug candidates has sharply increased. Then, the candidates excavated through the primary screening process (discovery and evaluation of target, and excavation of candidates) are subjected to a secondary screening process (optimization of candidates) which is much lower in yield than is the primary screening process. The difference of yield between the primary and secondary screening processes incurs a significant bottleneck phenomenon in the development of new drugs. Hence, it is an important challenge throughout new drug development to increase the efficiency of secondary screening to a level in harmony with the primary screening process without deteriorating the quality of data generated in the secondary screening.

High-content screening (HCS) can be defined as a "technology for functionally and complexly screening various targets inside living cells on the basis of highly temporally and spatially resolved fluorescence images." Among fundamental technologies of HCS are a cell-based assay, real-time fluorescent imaging of living cells with high temporal and spatial resolution, and a high-speed and high-content automated assay. Representative of HCS analysis instruments is the Opera system of Perkin-Elmer shown in FIG. 1. Formal cell analysis data obtained by the Opera system is as shown in FIG. 2. In this regard, first, images of tens of aggregated cells are obtained within a field, and cell nuclei and walls are discriminated among the images, during which images of some cells are removed on the program while leaving significant cell images. Finally, two-color images are obtained as seen in FIG. 2.

The high-content screening technology has been based on fluorescence assay, so far. However, fluorescent labels used in fluorescence assay weaken in fluorescence intensity (photobleaching), and exhibit interference between different fluorescent labels because excitation light with a very narrow wavelength range is used while the fluorescent light has a very broad range of wavelengths. In addition, there are an extremely limited number of available fluorescent substances.

Therefore, there is a need for a new method for effective high-speed drug screening that exhibits sharp spectrum peaks without causing interference between fluorescent substances, thus allowing the detection of multiple drugs.

In recent years, Raman spectroscopy has attracted extensive attention.

Inter alia, Surface Enhanced Raman Scattering (SERS) is a spectroscopic method which utilizes the phenomenon whereby, when molecules are adsorbed on a roughened surface of a metal nanostructure such as a gold or silver nanoparticle, the intensity of Raman scattering is dramatically increased to the level of $10^6 \sim 10^8$ times compared with normal Raman signals. As light passes through a transparent medium, molecules or atoms of the medium scatter the light. In this regard, a small fraction of the photons undergoes inelastic scattering, known as Raman scattering. For example, a fraction of the incident photons interact with the molecules in such a way that energy is gained or electrons are excited into higher energy levels, so that the scattered photons have a different frequency from that of the incident photons. Because the frequencies of the Raman scattering spectrum account for the chemical compositions and structural properties of the light absorbing molecules in a sample, Raman spectroscopy, together with the nanotechnology which is currently being quickly developed, can be further developed for highly sensitive detection of a single molecule. In addition, there is a strong expectation that an SERS sensor can be importantly used as a medical sensor. The SERS effect is in relation with plasmon resonance. In this context, metal nanoparticles exhibit apparent optical resonance in response to incident electromagnetic radiation due to the collective coupling of conduction electrons within the metal. Thus, nanoparticles of gold, silver, copper and other specific metals can fundamentally serve as nanoscale antenna for amplifying the localization of electromagnetic radiation. Molecules localized in the vicinity of these particles show far greater sensitivity to Raman spectroscopy.

Accordingly, many studies are being actively carried out about using SERS sensors to detect biomarkers including genes and proteins for early diagnosis of various diseases. Raman spectroscopy has various advantages over other methods (e.g., infrared spectroscopy). While infrared spectroscopy can detect strong signals from molecules which have a dipole moment, Raman spectroscopy allows strong signals to be detected even from non-polar molecules in which induced polarizability is modulated. Hence, almost all organic molecules have their own Raman shifts ($cm^{-1}$). In addition, being free from the interference of water molecules, Raman spectroscopy is suitable for use in the detection of biomolecules including proteins, genes, etc. Due to low signal intensity, however, the stage of development of Raman spectroscopy has not yet reached the level where it can be used in practice in spite of research spanning a long period of time.

Since its discovery, Surface-Enhanced Raman Scattering (SERS) has continually been developed to such a level so as to detect signals at a molecular level from randomized aggregates of fluorescent dye-absorbed nanoparticles (Science 1997, 275(5303), 1102; Phys rev lett 1997, 78(9), 1667). Since then, many studies of SERS enhancement with various nanostructures (nanoparticles, nanoshells, nanowires) have been reported. In order to utilize SERS as a highly sensitive detection method for a biosensor, Mirkin et al. reported highly sensitive DNA analysis by using DNA-modified gold nanoparticles, with a detection limit of 20 fM (2002, Science, 297, 1536). However, there have been almost no advances in preparing single molecule SERS active substrates based on the salt-induced aggregation of silver (Ag) nanoparticles having Raman active molecules (e.g., Rhodamine 6G) since the first study. A report has it that only a fraction (less than 1%) of heterogeneously aggregated colloids has single molecule SERS activity (J Phys Chem B 2002, 106(2), 311). Like this, randomly roughened surfaces provide a multitude of interesting essential data associated with SERS, but this strategy is fundamentally impossible to reproduce because even a small change in surface morphology leads to a significant change of enhancement. Recently, Fang et al. reported a quantitative measurement of the distribution of site enhancements in SERS. The hottest SERS-active sites ($EF>10^9$) accounted for only 63 sites out of a total of 1,000,000 sites, but contributed 24% to the overall SERS intensity (Science, 2008, 321, 388). In these regards, assembling SERS-active nanoparticles into well-defined and reproducible hot SERS nanostructures would lead to a highly reliable, sensitive assay for biomolecules and be greatly useful for use in xenodiagnosis and in vivo imaging techniques.

Leading to the present invention, intensive and thorough research into the high-speed screening of multiple drugs in association with Raman spectroscopy, conducted by the present inventors, resulted in the finding that when exposed to a sample containing one or more analytes, a nanoparticle labeled with an analyte-recognizing biomolecule functionalized thereon, comprising a core and a shell with a nanogap formed therebetween, is used to produce Raman signals if it is irradiated with an excitation laser beam, and that specific Raman wavelengths can be obtained from the Raman signals by filtration through multiple Raman filters, detected with a high SERS enhancement factor by a detector, and color coded to generate color-coded Raman images, whereby multiple drugs can be screened at high speeds with high reproducibility and reliable quantifiability.

DISCLOSURE

Technical Problem

It is an object of the present invention to provide a high-speed screening apparatus of multiple drugs using Raman spectroscopy by which multicolors are coded for Raman signals.

It is another object of the present invention to provide a high-speed screening method of multiple drugs, using the apparatus.

Technical Solution

The one object of the present invention may be accomplished by providing a high-speed screening apparatus of multiple drugs using surface-enhanced Raman scattering, comprising: an excitation module, composed of a lens, a mirror, and a pinhole, for introducing light from a light source into a microscope; a microscope module for acquiring an image of a sample, comprising a motion controller for controlling a position of the sample, a filtration unit composed of one or more Raman filters for filtering Raman wavelengths against light scattered from the sample when the sample is irradiated with excitation light from the light source, and a detector for sequentially receiving light beams passing through the filtration unit; and an image processing module for coding colors for a set of images obtained from a point containing a sample to produce cell or tissue images, and for displaying the cell or tissue images, said point being positioned by the motion controller. In one embodiment, the high-speed screening apparatus may further comprise a storage chamber for storing core-gap-shell nanoparticles.

The other object of the present invention may be accomplished by providing a high-speed screening method of multiple drugs using surface enhanced Raman scattering, comprising: adding the core-gap-shell nanoparticles of claim 10 to a sample to be analyzed (step 1); obtaining one or more Raman images from the sample by irradiating a laser beam on the sample to generate Raman scattered light, filtering the Raman scattered light through a filtration unit composed of one or more Raman filters to extract a Raman wavelength of interest, and detecting the Raman spectrum using a detector (step 2); and coding colors for the Raman images of the sample to generate cell or tissue images and displaying the cell or tissue images (step 3).

Advantageous Effects

As described hitherto, the screening apparatus and method of the present invention is not designed to detect autofluorescence, but to measure Raman signals generated from core-gap-shell nanoparticles, so that it exhibits no interference between fluorescent labels. The core-gap-shell nanoparticles show very strong surface-enhanced Raman scattering (SERS) signals, with an SERS enhancement factor of up to about $10^{12}$, and are proven to be highly reproducible. In addition, the use of a CCD camera as a detector allows the apparatus and method of the present invention to screen multiple drugs at a high speed because the CCD camera, which operates in a non-scanning manner, can photograph individual wells of well plates momentarily and can take pictures of other wells in association with the operation of the motion controller. Further, the apparatus and method of the present invention can code multiple colors for Raman images, and are effectively applicable to the screening of various drugs.

MODE FOR INVENTION

Figure 1:
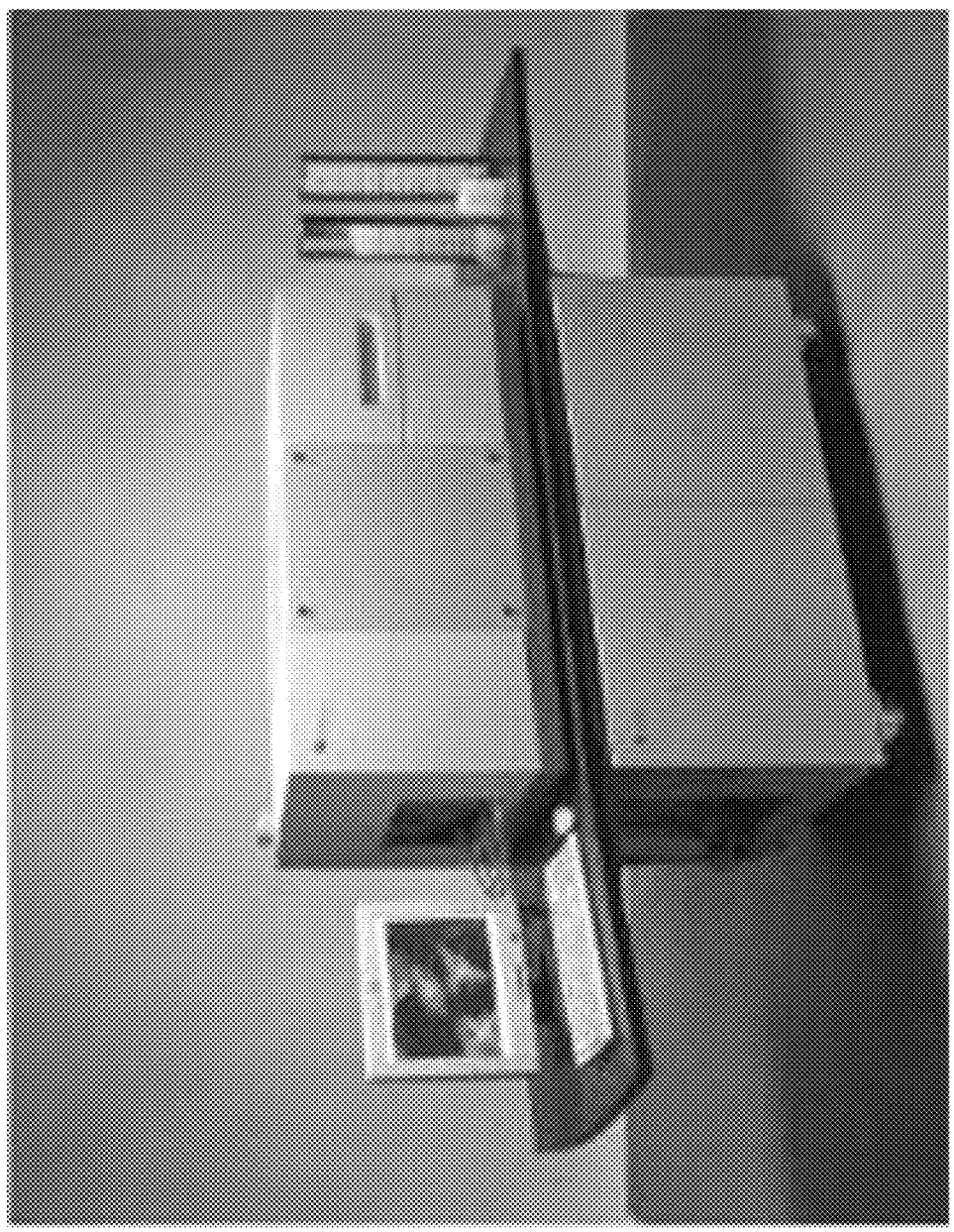
FIG. 1 is a photograph of a conventional fluorescence-based high-content screening analysis instrument.
Figure 2:
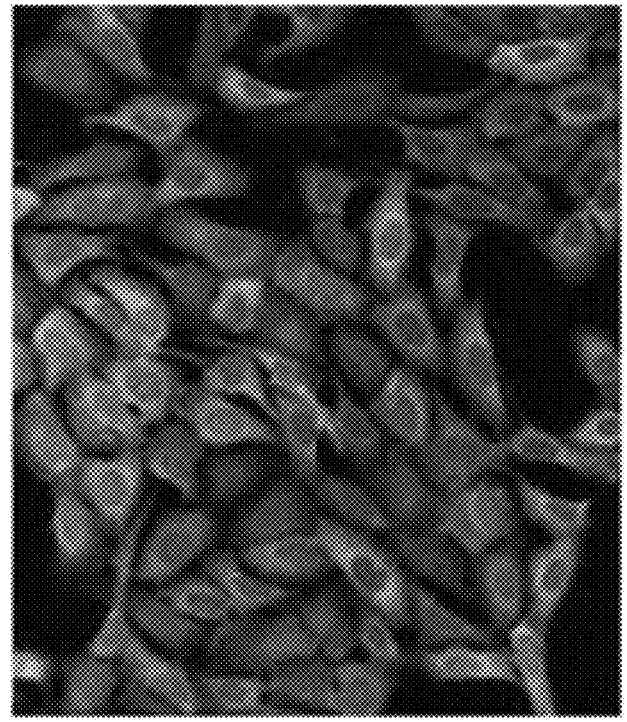
FIG. 2 is a 2-color image of cells obtained by a conventional fluorescence-based high-content screening analysis instrument.

Below, a detailed description will be given of the present invention.

In accordance with one aspect thereof, the present invention addresses a high-speed screening apparatus of multiple drugs using surface-enhanced Raman scattering, comprising:

an excitation module, composed of a lens, a mirror, and a pinhole, for introducing light from a light source into a microscope;

a microscope module for acquiring an image of a sample, comprising a motion controller for controlling a position of the sample, one or more Raman filters for filtering Raman wavelengths against light scattered from the sample when the sample is irradiated with excitation light from the light source, and a detector for sequentially receiving light beams passing through the Raman filters; and an image processing module for coding colors for one or more images obtained at a point containing a sample to produce cell or tissue images, and for displaying the cell or tissue images.

Below, a description will be given of preferred embodiments of the present invention in conjunction with FIG. 3.

Throughout the accompanying drawings, the same reference numerals are used to designate the same or similar components. Further, in the description of the present invention, when it is determined that the detailed description of the related art would obscure the gist of the present invention, the description thereof will be omitted.

Figure 3:
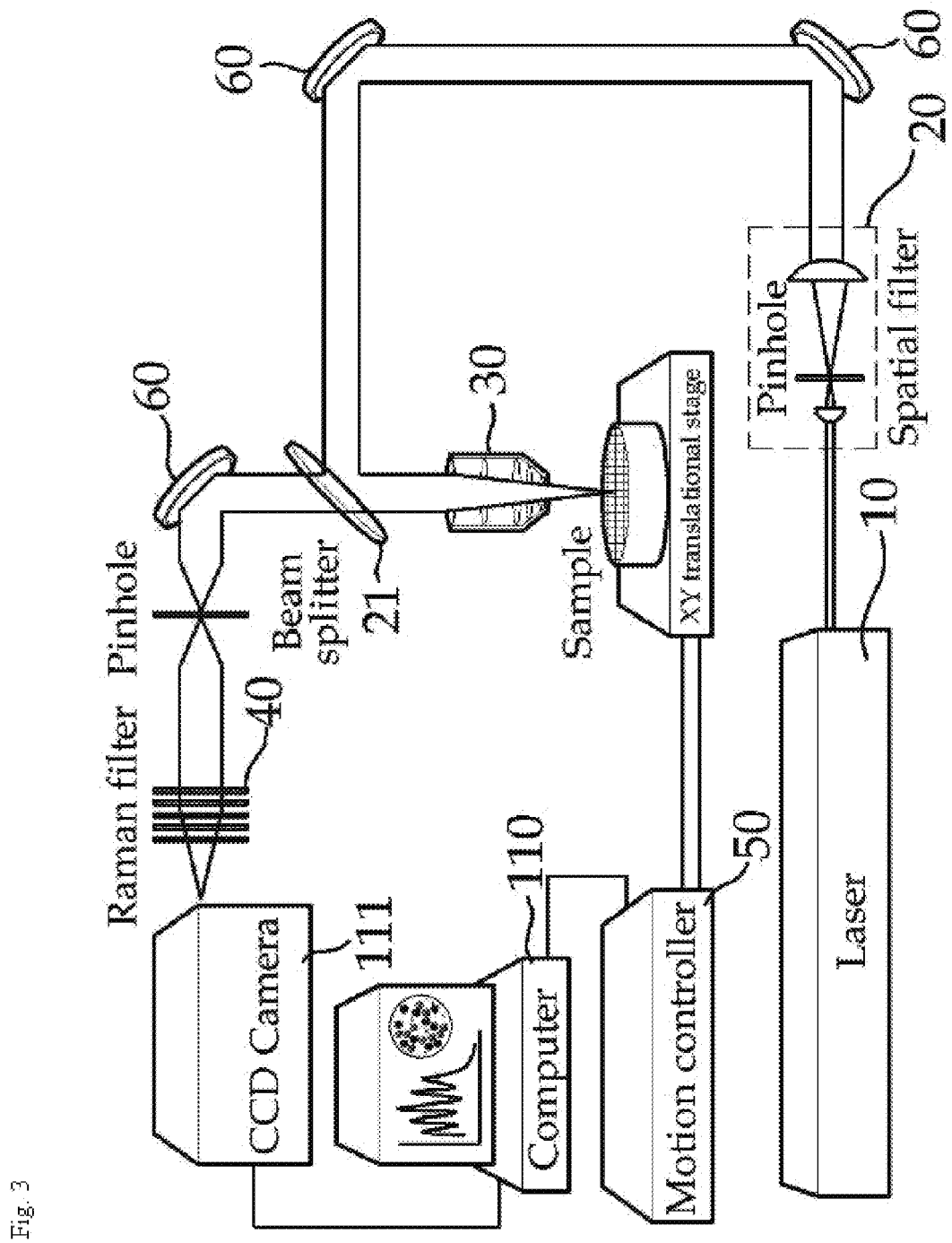
FIG. 3 is a conceptual view of a Raman-based high-speed screening apparatus of multiple drugs according to the present invention.

FIG. 3 is a conceptual view of a Raman-based high-speed screening apparatus of multiple drugs according to the present invention.

The Raman-based high speed screening apparatus of multiple drugs according to the present invention may be divided into an excitation module, a microscope module, and an image processing module. It should be apparent to those skilled in the art that the functional modules are intended simply for concrete descriptions thereof, but not to divide them into exclusive and independent parts, and that the functional modules may be overlapped in certain regions or two or more functional modules may participate in one region.

Excitation Module

In the apparatus of the present invention, the excitation module functions to introduce a laser beam generated from a light source (LS) 10 into a microscope.

The LS 10 may generate a near infrared (NIR) laser or a visible laser. The visible laser is light with a wavelength of from 400 to 700 nm. In one embodiment, the visible laser has a wavelength of 514.5 nm. In the biotechnology field, Raman images have been obtained mainly using an NIR laser since the use of visible light as a light source induces autofluorescence, which brings about a reduction in the intensity of Raman signals. However, because Raman signal strength is in inverse proportion to a fourth power of wavelength, a visible laser can increase the intensity of Raman signals further than can an NIR laser. In addition, optical devices utilizing visible light are more advanced than those using NIR light. Hence, if it can reduce autofluorescence, the use of visible lasers has an advantage over that of NIR lasers in optimizing an optical system.

After being generated by the LS 10, a laser beam passes through a spatial filter 20 so that the beam diameter expands. Through a plurality of lenses, a mirror, and a pinhole, the beam is collimated to have a diameter of about 10 mm, and then introduced into a microscope module.

Microscope Module

In the apparatus of the present invention, the microscope module comprises a motion controller 50 for controlling the position of a sample, a Raman filtration unit 40 consisting of one or more Raman filters for filtering Raman wavelength light against scattered light from the sample when the sample irradiated with excitation light from a laser beam, and a detector 111 for sequentially receiving light beams passing through the Raman filtration unit 40.

After entry into a microscope, the laser beam is reflected by a light separation unit 21 and is directed toward a microscope objective (MO) lens 30. As the light separation unit 21, a beam splitter, a dichroic mirror, or a detachable mirror may be used.

The number of the Raman filters for filtering Raman wavelength light is in the order of 1 to 20, and preferably in the order 5 to 20.

The Raman filtration unit may be a band pass filter, and preferably includes, but is not limited to, a narrow band pass filter.

So long as it operates as a scanning type or non-scanning type, any detector may be employed in the present invention. For example, PMT (photomultiplier tube) detectors or APD (avalanche photodiode) detectors, all operating in a scanning manner, may be employed, while a CCD (charge-coupled device) camera is representative of available detectors operating in a non-scanning manner.

Figure 4:
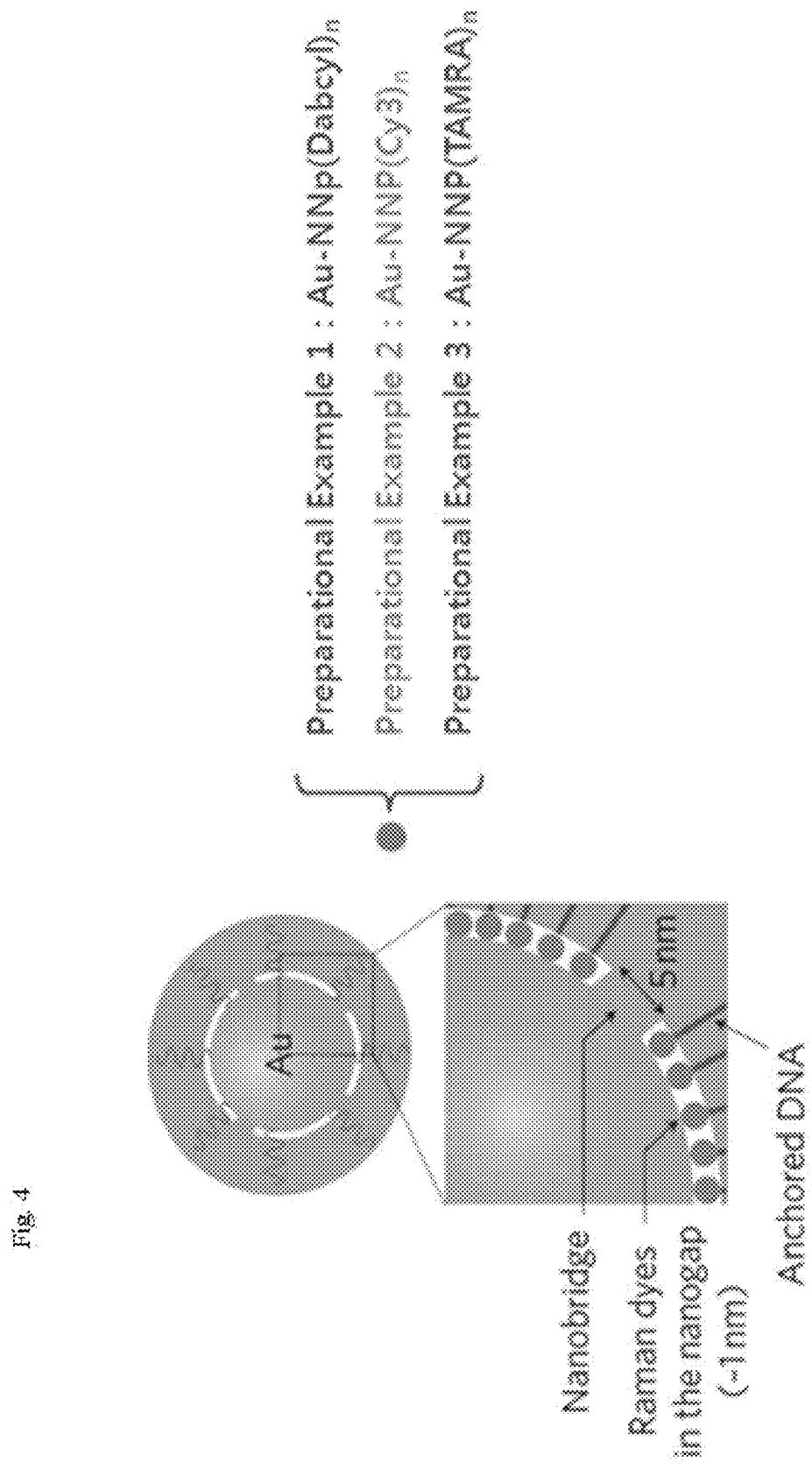
FIG. 4 shows a core-gap-shell nanoparticle useful for the Raman spectroscopy-based high-speed screening method of multiple drugs.

The sample may be a cell containing an analyte. Examples of the analyte of interest include amino acids, peptides, polypeptides, proteins, glycoproteins, lipoproteins, nucleosides, nucleotides, oligonucleotides, nucleic acids, saccharides, carbohydrates, oligosaccharides, polysaccharides, fatty acids, lipids, hormones, metabolites, cytokines, chemokines, receptors, neurotransmitters, antigens, allergens, antibodies, substrates, metabolites, co-factors, inhibitors, drugs, pharmaceuticals, nutrients, prions, toxins, poisons, explosives, pesticides, chemical warfare agents, biohazardous agents, radioisotopes, vitamins, heterocyclic aromatic compounds, carcinogens, mutagens, narcotics, amphetamines, barbiturates, hallucinogens, waste products and contaminants. In addition, when the analyte is a nucleic acid, it may be exemplified by genes, viral RNA and DNA, bacterial DNA, fungal DNA, mammalian DNA, cDNA, mRNA and DNA fragments, oligonucleotides, synthetic oligonucleotides, modified oligonucleotides, single- and double-stranded nucleic acids, and natural and synthetic nucleic acids. Separately, the sample may be associated with a core-gap-shell nanoparticle shown in FIG. 4 so as to amplify Raman signals. The association may be achieved by exposing core-gap-shell nanoparticles stored in a chamber (not shown) of the apparatus to the sample.

The core-gap-shell is designed to have a biomolecule functionalized on the surface of the shell which can recognize the analyte of interest. When the core-gap-shell nanoparticles are exposed to a sample, they selectively bind to the analyte of interest and can be ready for imaging.

Among the biomolecules functionalized on the nanoparticles may be antibodies, antibody fragments, genetically modified antibodies, single-chain antibodies, receptor proteins, ligand proteins, enzymes, inhibitor proteins, lectins, cell adhesion proteins, oligonucleotides, polynucleotides, nucleic acids, and aptamers. Functionalization may be accomplished by, but is not limited to, attaching a biomolecule onto a nanoparticle via an electrostatic force, or by binding a biomolecule to a nanoparticle directly or via a linker.

In the present invention, the core-gap-shell nanoparticle comprises a core, a shell surrounding the core, and a nanogap formed between the core and the shell. In the nanoparticle, the core is connected with the shell via a nanobridge or is not connected with the shell, with the nanogap containing an optically active molecule therein.

So long as it consists of an atom selected from among C, H, O, N, S, and a combination thereof, any optically active molecule may be used in the present invention. In addition, a metal ion, a chelator of metal ions, or a metal nanoparticle may be employed. In detail, a signal substance used in the present invention is a broad concept encompassing fluorescent organic molecules, non-fluorescent organic molecules, inorganic nanoparticles, and Raman active molecules, and refers to a chromogenic labeling substance without limitations imparted thereto. Preferred is a Raman active molecule. As used herein, the term "Raman active molecule" refers to a molecule that facilitates the detection and measurement of an analyte by a Raman detection apparatus after the nanoparticle of the present invention is bound to at least one analyte. Raman active molecules available for Raman spectroscopy may be organic atoms or molecules, or inorganic atoms or molecules. Examples of the Raman active molecules useful in the present invention include, but are not limited to, FAM, Dabcyl, TAMRA, TRITC (tetramethyl rhodamine-5-isothiocyanate), MGITC (malachite green isothiocyanate), XRITC (X-rhodamine-5-isothiocyanate), DTDC (3,3-diethylthiadicarbocyanine iodide), TRIT (tetramethyl rhodamineisothiol), NBD (7-nitrobenz-2-1,3-diazole), phthalic acid, terephthalic acid, isophthalic acid, para-aminobenzoic acid, erythrosine, biotin, digoxigenin, 5-carboxy-4',5'-dichloro-2',7'-dimethoxy, fluorescein, 5-carboxy-2',4',5',7'-tetrachlorofluorescein, 5-carboxyfluorescein, 5-carboxyrhodamine, 6-carboxyrhodamine, 6-carboxyteteramethyl aminophthalocyanine, azomethine, cyanines (Cy3, Cy3.5, Cy5), xanthine, succinylfluorescein, aminoacridine, quantum dots, carbon isotopes, cyanides, thiols, chlorine, bromine, methyls, phosphorous, and sulfur. For use in the nanostructure of the present invention, the Raman active molecule is required to show a clear Raman spectrum and must be associated or related with different kinds of analytes. Preferred are molecules that detect higher Raman signals by being resonant with excitation laser wavelengths used for Raman analysis.

The optical active molecule may be confined within the nanogap. In this regard, the optically active molecule is modified via a covalent bond or electrostatic attraction with the biomolecule functionalized on the nanoparticle so that it is positioned in an interior gap. Alternatively, the optically active molecule may be attached onto the surface of the core particle via a covalent bond or electrostatic attraction irrespective of the biomolecule. Modification with the biomolecule has the advantage of controlling the position of the optically active molecule. In detail, if it is modified at a position near the end of the biomolecule attached onto the core, the optically active molecule may be located near the core. In this manner, the optically active molecule can be positioned within the nanogap. Raman signals may vary depending on the position of the optically active molecule. For example, when the optically active molecule is positioned in the interior gap, the strongest Raman signals can be detected, with high uniformity and reproducibility.

Herein, kinds of the optically active molecule confined within the nanogap of the core-gap-shell determine certain Raman peaks generated. The Raman peaks are detected through corresponding Raman filters by a detector, such as CCD, to acquire images of the sample (cell). These images are color coded by a computer program and then displayed.

The term "core," as used herein, refers to a spherical or sphere-like particle with a diameter of 1~900 nm, consisting of a metal exhibiting surface plasmon resonance, such as gold, silver or copper.

As used herein, the term "shell" refers to a coating layer surrounding the core, composed of a metal exhibiting surface plasmon resonance. The shell ranges in thickness from 0.1 to 900 nm and preferably from 1 nm to 100 nm. Between the core and the shell, a space, called a nanogap, is formed. Gold, silver or copper may be used as the metal exhibiting surface plasmon resonance.

As used herein, the term "nanogap" means a space formed between the core and the shell. The thickness of the nanogap is preferably in the order of 0.01 to 100 nm. The core may be discriminated from the shell by the nanogap. The core and the shell may not contact each other where the nanogap is formed while contacting each other through a nanobridge. That is, the "nanogap" does not mean a space by which the core and the shell are completely separated from each other.

The term "nanobridge," as used herein, refers to a bridge with a diameter of 0.5 to 20 nm through which the core is connected with the shell. The nanoparticle may comprise a "nanobridged nanogap" or a "nanobridgeless nanogap."

The term "optically active molecule," as used herein, refers to a molecule that produces Raman scattering beams in response to excitation light. Located between the core and the shell, both exhibiting surface plasmon resonance, the optically active molecule exerts a maximum surface-enhanced Raman scattering effect.

In accordance with a preferred embodiment of the present invention, the core-gap-shell nanoparticle may be selected from the group consisting of i) a nanoparticle consisting of a gold core and a silver shell with a nanogap formed between the gold core and the silver shell, ii) a nanoparticle consisting of a silver core and a gold shell with a nanogap formed between the silver core and the gold shell, iii) a nanoparticle consisting of a gold core and a gold shell with a nanogap formed between the gold core and the gold shell, and iv) a nanoparticle consisting of a silver core and a silver shell with a nanogap formed between the silver core and the silver shell. Most preferable is a nanoparticle consisting of a gold core and a gold shell with a nanogap formed therebetween. No particular limitations are imparted to the morphology of the core.

In the nanoparticle, the core may be connected with the shell via a nanobridge. That is, a shell may be established over the core in such a way that the shell touches the core surface in some parts to form nanobridges, and the nanobridged nanogap is formed along the core surface. The number of nanobridges is not particularly constrained so long as it guarantees the formation of the nanogap. Preferably, the nanobridge has a diameter of from 0.5 nm to 20 nm. The nanobridge functions to stably maintain the core-shell structure and increase the signal of SERS.

The optically active molecule, positioned in the nanogap between the core and the shell, exerts a maximum surface-enhanced Raman scattering (SERS) effect with the help of the plasmonic coupling at the nanogap between the core and the shell, thereby amplifying Raman signals. Particularly, the nanogap structure can be synthesized with high reproducibility. In addition, the nanogap structure brings about exceptional improvements in the quantifiability of signals, the reproducibility of data, the ease and convenience of synthesis, the expense, and the stability of probes.

The light emitted from the sample transverses the light separation unit 21 and then travels toward the Raman filtration unit 40 before detection by the detector 111.

The Raman filtration unit may comprise one or more Raman filters through which only specific Raman wavelengths can pass, preferably 1 to 20 Raman filters, and more preferably 5 to 20 Raman filters. The light with different Raman wavelengths, emitted from the sample, passes through a series of Raman filters for respective Raman wavelengths, so that specific Raman wavelengths are detected by the detector to obtain 1 to 20 multiple images.

As stated above, the Raman filtration unit may employ a band pass filter, and preferably a narrow band pass filter.

The detector 111, for example, a CCD camera operating in a non-scanning manner, may be provided with a zoom lens to adjust magnification. Given a zoom lens, the detector can be improved in optical microscopic function, and allows for the observation of more concrete optical images.

Turning to the motion controller 50, it functions to locate the sample at a precise position fit to the focal point of the incident light by moving a stage on which a well plate containing the sample is loaded in the X or Y axis direction. After multiple images are obtained from one point (well) containing the sample according to the number of the Raman filters, another point is moved into the focal point by the motion controller 50 and is used for Raman imaging. In association with the motion controller, a detector operating in a non-scanning manner, for example, a CCD (charge-coupled device), can take Raman images from individual wells at a high speed, thus allowing for high-speed screening.

In addition, the microscope module may be provided with an atmosphere maintainer (not shown) for maintaining the atmosphere of the external chamber in which the sample is positioned. The atmosphere maintainer may control conditions of the chamber, such as temperature, humidity, pH and the like.

Image Processing Module

The image processing module functions to code colors for the single or plural Raman images obtained from the points, to convert the color-coded Raman images into cell or tissue images, and to display the cells or tissue images.

Preferably, the image processing module is a computer. The data obtained in the CCD camera is processed, and may be stored in a main memory unit. Data on emission profiles for standard analytes may also be stored in a main memory or ROM. The processor may compare emission spectra from analytes on a Raman-active substrate to discriminate kinds of the analytes. In addition, the processor analyzes the data from the detector to determine identities and/or concentrations of various analytes. In the image processing module, different computers may be used for respective specific tasks. Thus, different system structures may be employed in different embodiments of the present invention. After collection thereof, the data is subjected to analysis. To facilitate data analysis, a high-performance digital computer may be recruited. The computer may be suitably programmed for analyzing and reporting collected data in addition to accommodating and storing the data.

Respective different colors are coded for one or more Raman peaks detected through one or more Raman filters using software. The color-coded Raman images thus obtained are converted into and displayed as images of cells or biotissues on a monitor.

As described above, the apparatus of the present invention can generate highly-resolved, surface-enhanced Raman scattering (SERS) spectra from one or more analytes present in a sample (e.g. cells) after one or more core-gap-shell nanoparticles are selectively associated with the analytes. When employing a detector operating in a non-scanning manner, for example, a CCD (charge-coupled device) camera, the apparatus of the present invention can screen multiple drugs at a high speed because the CCD camera can photograph many wells within a short period of time in concert with the operation of the motion controller.

It should be apparent to those skilled in the art that although many specified elements such as concrete components are elucidated with reference to the drawings illustrating the apparatus of the present invention, those skilled in the art will appreciate that various modifications, additions and substitutions are possible, without departing from the scope and spirit of the invention.

In accordance with another aspect thereof, the present invention addresses a method for screening multiple drugs at a high speed using surface enhanced Raman scattering, comprising:

adding the core-gap-shell nanoparticles to a sample to be analyzed (step 1);

obtaining one or more Raman images from the sample by irradiating a laser beam on the sample to generate Raman scattered light, filtering the Raman scattered light through one or more Raman filters to extract a Raman wavelength of interest, and detecting the Raman spectrum using a detector (step 2); and coding colors for the Raman images of the sample to generate cell or tissue images and displaying the cell or tissue images (step 3).

In step 1, a reagent containing core-gap-shell nanoparticles is added to a sample comprising cells.

For use in step 1, the core-gap-shell nanoparticles are designed to have a biomolecule, capable of recognizing an analyte of interest, which is functionalized on the surface of the shell. When the core-gap-shell nanoparticles are exposed to a sample, the biomolecule binds to the analyte of interest, and thus can be ready for Raman imaging.

As described above, the core-gap-shell nanoparticle may be selected from the group consisting of i) a nanoparticle consisting of a gold core and a silver shell with a nanogap formed between the gold core and the silver shell, ii) a nanoparticle consisting of a silver core and a gold shell with a nanogap formed between the silver core and the gold shell, iii) a nanoparticle consisting of a gold core and a gold shell with a nanogap formed between the gold core and the gold shell, and iv) a nanoparticle consisting of a silver core and a silver shell with a nanogap formed between the silver core and the silver shell. Most preferable is a nanoparticle consisting of a gold core and a gold shell with a nanogap formed therebetween.

In step 1, exposure of the core-gap-shell nanoparticles to an analyte may be performed inside or outside the screening apparatus of the present invention.

Step 2 is designed to produce and capture one or more Raman images of the analyte of interest. In this regard, a laser beam is irradiated on the sample to generate Raman scattered light which is then directed toward one or more Raman filters. After passage through the Raman filters, specific Raman wavelengths are detected by a detector, for example, a CCD camera.

In the screening apparatus of the present invention, the Raman filtration unit may comprise one or more Raman filters through which only specific Raman wavelengths can pass, preferably 1 to 20 Raman filters, and more preferably 5 to 20 Raman filters. The light with different Raman wavelengths, emitted from the sample, passes through a series of Raman filters for respective Raman wavelengths, so that specific Raman wavelengths are detected by the detector to obtain 1 to 20 multiple images As stated above, the Raman filtration unit may employ a band pass filter, and preferably a narrow band pass filter.

The detector, for example, a CCD camera, may be provided with a zoom lens to adjust the magnification. Given a zoom lens, the detector allows for the observation of optical images in more detail.

Next, in step 3, colors are coded for the Raman images obtained in step 2, and the color-coded Raman images are converted into cell or tissue images which are then presented on a display.

According to Raman peaks, 1 to 20 colors are coded for the Raman images obtained in step 2 to produce color-coded Raman images ranging in multiplexity from 1 to 20 colors.

Designed not to detect autofluorescence but to measure Raman signals generated from core-gap-shell nanoparticles, the screening apparatus and method of the present invention exhibit no interference between fluorescent labels. The core-gap-shell nanoparticles show very strong surface-enhanced Raman scattering (SERS) signals, with an SERS enhancement factor of up to about $10^{12}$, and are proven to be highly reproducible. In addition, the use of a CCD camera as a detector allows the apparatus and method of the present invention to screen multiple drugs at a high speed because the CCD camera, which operates in a non-scanning manner, can photograph individual wells of well plates momentarily, and can take pictures of other wells in association with the operation of the motion controller. Further, the apparatus and method of the present invention can code multiple colors for Raman images, and is effectively applicable to the screening of various drugs.

A better understanding of the present invention may be obtained through the following examples which are set forth to illustrate, but are not to be construed as limiting the present invention.

SYNTHESIS EXAMPLES 1 to 3

Synthesis of Core-Gap-Shell Nanoparticles

A DNA strand was used as a Raman-dye modification platform with highly accurate position-controlling capability to synthesize an NNP (nanobridged nanogap particle) with a nanobridge-supported interior gap, as follows.

DNA-modified gold nanoparticles (20 nm in diameter; DNA sequences: [3'-HS—$(CH_2)_3$-(Dabcyl)-$A_{10}$-$PEG_{18}$-AAACTCTTTGCGCAC-5'] for Synthesis Example 1, [3'-HS—$(CH_2)_3$-(Cy3)-$A_{10}$-$PEG_{18}$-AAACTCTTTGCGCAC-5'] for Synthesis Example 2, and [3'-HS—$(CH_2)_3$-(TAMRA)-$A_{10}$-$PEG_{18}$-AAACTCTTTGCGCAC-5'] for Synthesis Example 3) were prepared according to literature procedures (S. J. Hurst, A. K. R. Lytton-Jean, C. A. Mirkin, Anal. Chem. 78, 8313 (2006)). To form gold shells around these DNA-modified gold nanoparticle cores, DNA-modified gold nanoparticles in a phosphate-buffered solution (0.3 M NaCl, 10 mM PB, pH 7.4) were reacted with a gold precursor ($HAuCl_4$, a reductant ($NH_2OH$—HCl) and 1% poly-N-vinyl-2-pyrrolidone (PVP; MW 40,000), followed by gently vortexing at room temperature for 30 min. Amounts of the gold precursor and the reductant were controlled based on the amount of the seeds (DNA-modified gold nanoparticles, 1 nM) to monitor a nanoparticle morphology change during the course of gold shell formation.

In this regard, the DNA-modified gold nanoparticle solution (100 μL; 1 nM in 0.3 M PBS) was mixed with 50 μL of a 1% PVP solution. The resulting solution was then mixed with 1.5, 5.2, 10.3 or 30.4 μL of hydroxylamine hydrochloride solution (10 mM) and 1.5, 5.2, 10.3 or 30.4 μL of chloroauric acid solution (5 mM), respectively. Depending on the amount of reagents used, various nanostructures were formed.

SYNTHESIS EXAMPLES 4 to 6

Synthesis of PEG-Coated Core-Gap-Shell Nanoparticles

Figure 9:
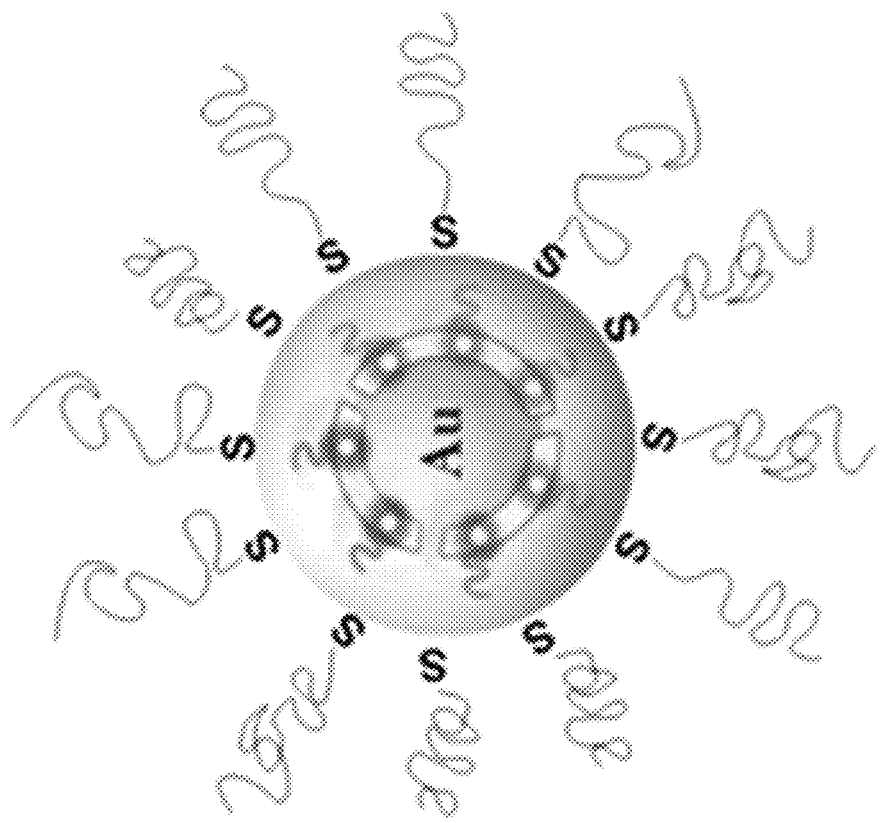
FIG. 9 is a schematic diagram of a PEG-coated nanoparticle synthesized in Synthesis Example 4, 5 or 6.

PEG was applied to the shell surface of each of the nanoparticles synthesized in Synthesis Examples 1 to 3 so as to render the particles well-dispersible in a cell culture media and thus more suitable for use in cellular experiments ("Dabcyl" (Synthesis Example 4), "Cy3" (Synthesis Example 5), "TAMRA" (Synthesis Example 6); refer to FIG. 9).

mPEG-SH (MW ~5 kDa) was applied to the shell surface of the nanoparticles to prepare PEG-coated gold-silver core-shell nanoparticles (Synthesis Examples 4 to 6) with reference to 'W. Peter Wuelfing, Stephen M. Gross, Deon T. Miles, and Royce W. Murray, *J. Am. Chem. Soc.* 120, 12696 (1998)'.

EXPERIMENTAL EXAMPLE 1

Evaluation of Surface-Enhanced Raman Scattering Spectrum

SERS spectra were recorded by the apparatus of the present invention, that is, the in-house nano-Raman spectroscope equipped with an inverted optical microscope (Axiovert 200, Zeiss) using the nanoparticles synthesized in Synthesis Examples 1 to 3.

First, 20 μL of each of the solutions containing the nanoparticles of Synthesis Examples 1 to 3 was applied to a cover glass slip by spin coating to construct a sample for spectral measurement. An excitation laser beam with a wavelength of 660 nm was directed at an energy of from 50 nW to 1 mW into an oil-immersion microscope objective (×100, 1.3 numerical aperture; ×50, 0.5 numerical aperture; Zeiss), which focuses the beam into the sample to generate Raman signals. The background Raman signals were collected on a liquid-nitrogen-cooled (−125° C.) CCD (charge-coupled device). All of the data was baseline-corrected to afford SERS spectra. The results are shown in FIG. 5.

Figure 5:
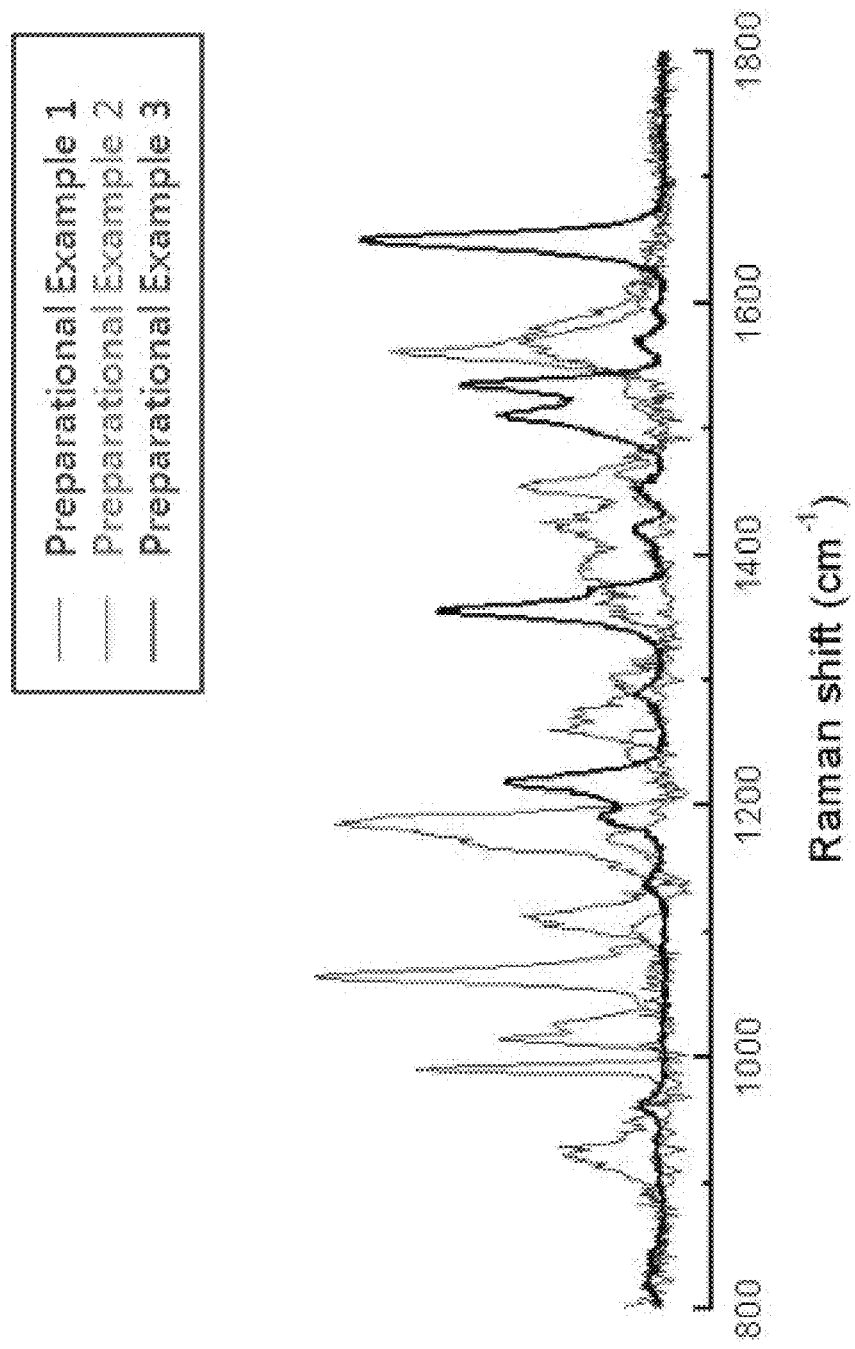
FIG. 5 shows surface-enhanced Raman scattering spectra measured by the apparatus of the present invention using nanoparticles synthesized in Synthesis Examples 1 to 3.

FIG. 5 shows surface-enhanced Raman scattering spectra recorded by the apparatus of the present invention using nanoparticles synthesized in Synthesis Examples 1 to 3.

As can be seen in the SERS spectra of FIG. 5, the nanoparticles synthesized in Synthesis Examples 1 to 3 generate their respective inherent Raman peaks.

In addition, in order to search for narrow band pass filters which selectively pass the Raman light scattered from the solutions containing the nanoparticles of Synthesis Examples 1 to 3 therethrough, the spectra obtained using an excitation laser of 660 nm were divided in nm units on the X-axis to determine the detail specifications of narrow band pass filters for filtering peaks and signals selected from the Raman spectra of the nanoparticles of Synthetic Examples 1 to 3, and the results are given as follows.

Figure 6:
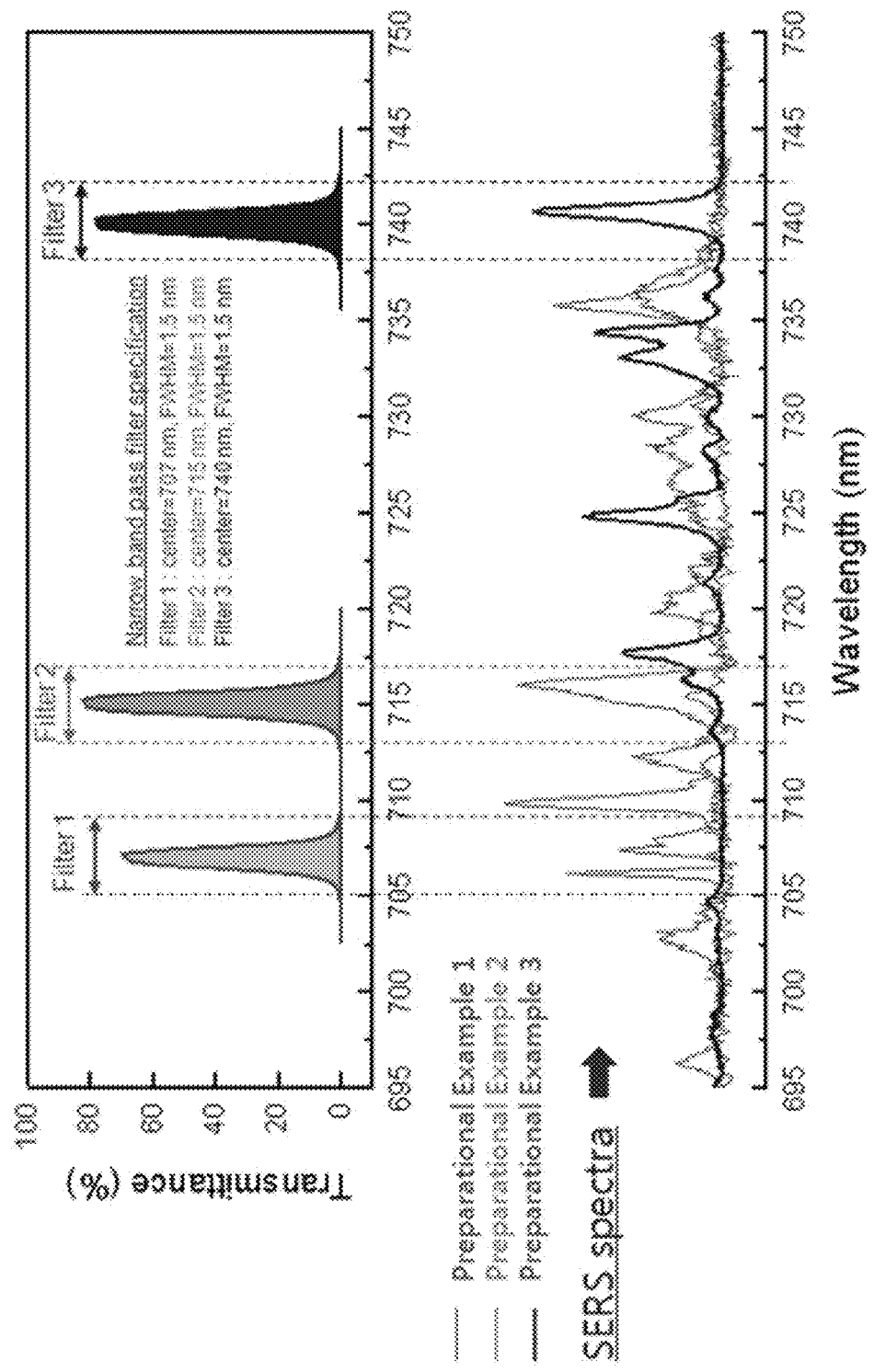
FIG. 6 shows wavelength ranges of narrow band pass filters for selectively filtering Raman light scattered from the nanoparticles of Synthesis Examples 1 to 3.

"Filter 1," optimized to nanoparticles of Synthetic Example 1: center=707 nm, FWHM=1.5 nm "Filter 2," optimized to nanoparticles of Synthetic Example 2: center=715 nm, FWHM=1.5 nm "Filter 3," optimized to nanoparticles of Synthetic Example 3: center=740 nm, FWHM=1.5 nm FIG. 6 shows wavelength ranges of narrow band pass filters for selectively filtering Raman light scattered from the nanoparticles of Synthesis Examples 1 to 3.

As is understood from the data of FIG. 6, the nanoparticles synthesized in Synthesis Examples 1 to 3 have respective inherent Raman wavelength ranges, which enable the establishment of narrow band pass filters optimized to the nanoparticles.

Further, to examine whether the nanoparticles synthesized in Synthesis Examples 1 to 3 are selectively imaged only by specific narrow band pass filters, an excitation laser of 660 nm was irradiated on solutions of the nanoparticles synthesized in Synthesis Examples 1 to 3, and the Raman light was sequentially directed towards the narrow band pass filters ("Filter 1", "Filter 2" and "Filter 3"). The results are given in FIG. 7. In addition, respective images obtained from the nanoparticles of Synthesis Examples 1 to 3 through narrow band pass filters optimized thereto were merged, and the results are given in FIG. 8.

Figure 7:
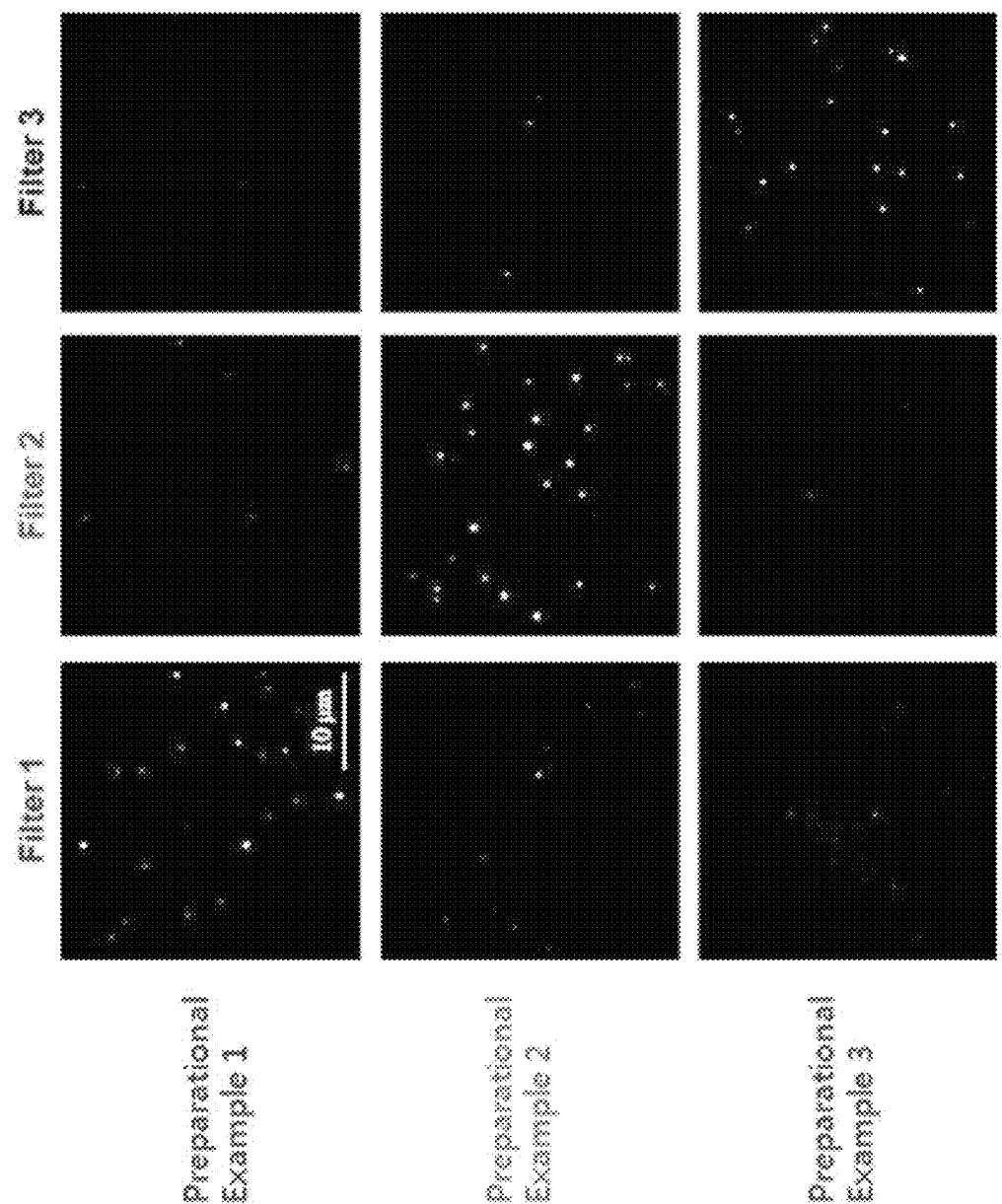
FIG. 7 shows Raman images detected after the selective filtration of Raman signals scattered from the nanoparticles synthesized in Synthesis Examples 1 to 3 through respective narrow band pass filters.

FIG. 7 shows Raman images detected after the selective filtration of Raman signals scattered from the nanoparticles synthesized in Synthesis Examples 1 to 3 through respective narrow band pass filters.

Figure 8:
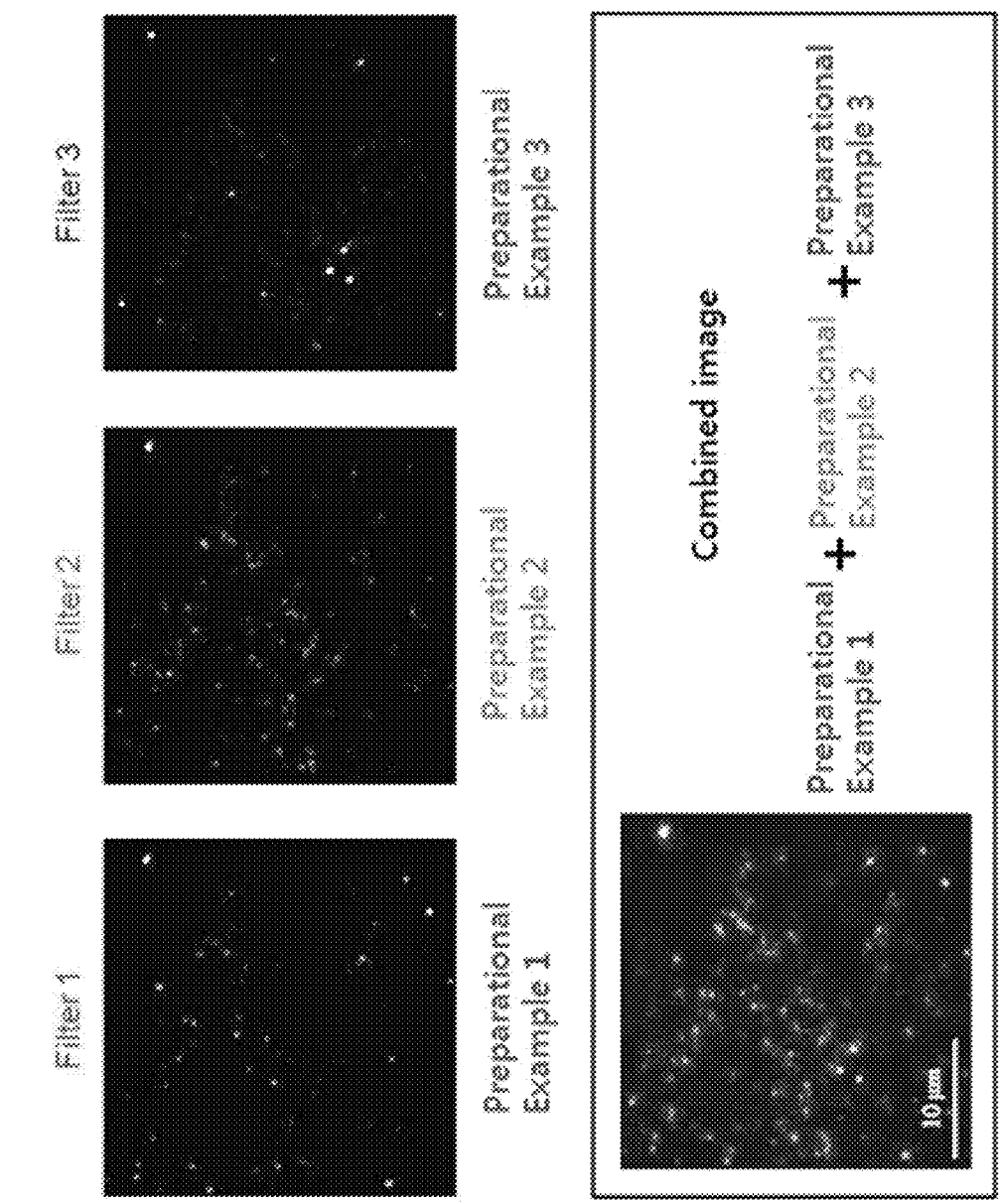
FIG. 8 shows Raman images selectively filtered through respective narrow band pass filters optimized for the nanoparticles of Synthesis Examples 1 to 3, and a merged image thereof.

FIG. 8 shows Raman images selectively filtered through respective narrow band pass filters optimized for the nanoparticles of Synthesis Examples 1 to 3, and a merged image thereof.

As is apparent from data of FIGS. 7 and 8, the nanoparticles synthesized in Synthesis Examples 1 to 3 were selectively imaged only when the narrow band pass filters optimized thereto were employed. Moreover, a Raman image was obtained by merging the Raman scattered beams obtained from the nanoparticles of Synthesis Examples 1 to 3.

EXPERIMENTAL EXAMPLE 2

Evaluation of Multicolor-Coded Cell Image

Multicolor-coded cell images were obtained by the apparatus of the present invention using the nanoparticles synthesized in Synthesis Examples 4 and 5.

In this regard, HeLa cells (cervix adenocarcinoma cell line) was seeded at a density of 20,000 cells/well into 96-well plates and maintained for 20~24 hrs in an incubator. Then, the cells were washed with PBS and incubated for 6 hrs with a cell medium containing the nanoparticles synthesized in Synthesis Example 4 or 5 in an incubator. The cells were again washed with PBS, and fixed for 15 min with a chilled fixation buffer (BD Cytofix™). After removal of the fixation buffer, the cells were washed twice with PBS, and stored in PBS in a refrigerator until use. A 660 nm excitation laser was irradiated onto the samples to generate Raman scattered beams which were allowed to pass through the narrow band pass filters ("Filter 1" and "Filter 2"). The resulting images are given in FIGS. 10 to 12.

Figure 10:
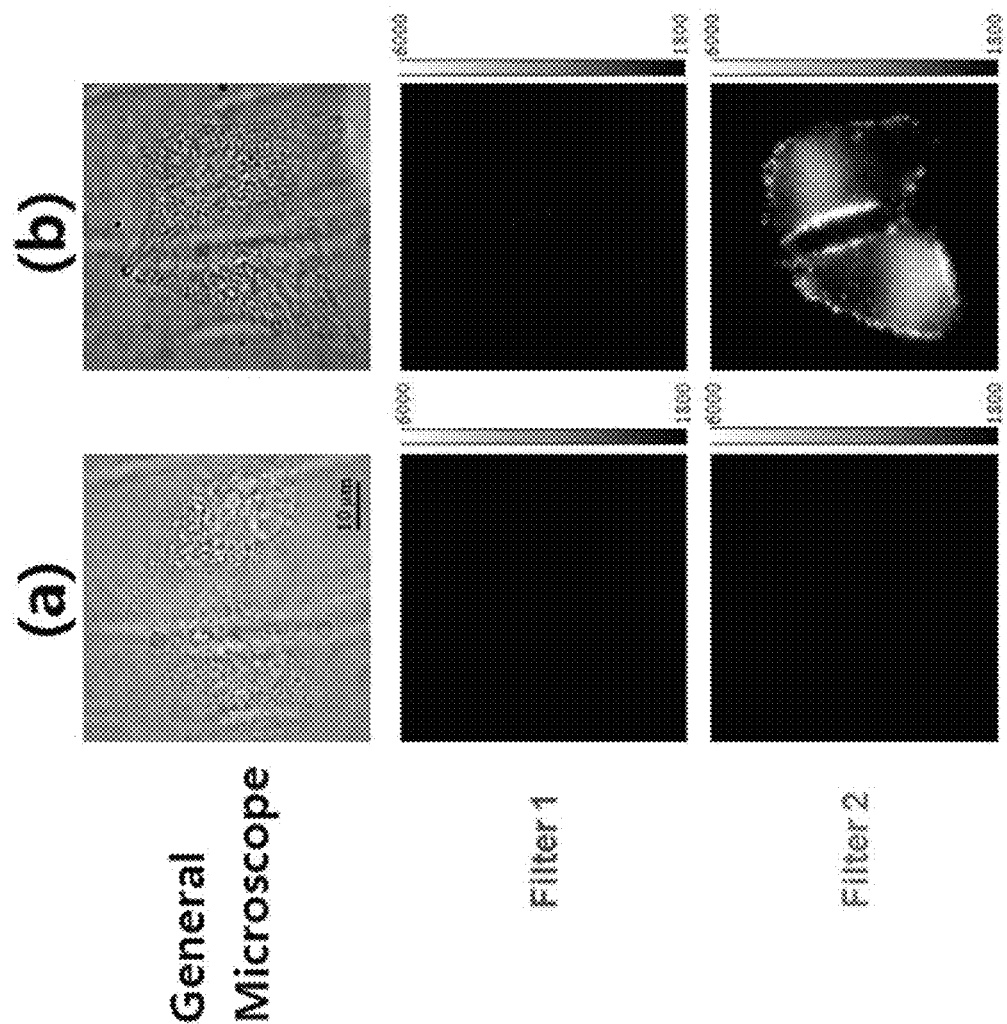
FIG. 10 shows images of cells incubated without (a) (control) and with (b) (test group) the PEG-coated nanoparticles synthesized in Synthesis Example 5, as measured by the apparatus of the present invention using two narrow band pass filters ("Filter 1" and "Filter 2").

FIG. 10 shows images of cells incubated without (a) (control) and with (b) (test group) the PEG-coated nanoparticles synthesized in Synthesis Example 5, as measured by the apparatus of the present invention using two narrow band pass filters ("Filter 1" and "Filter 2").

Figure 11:
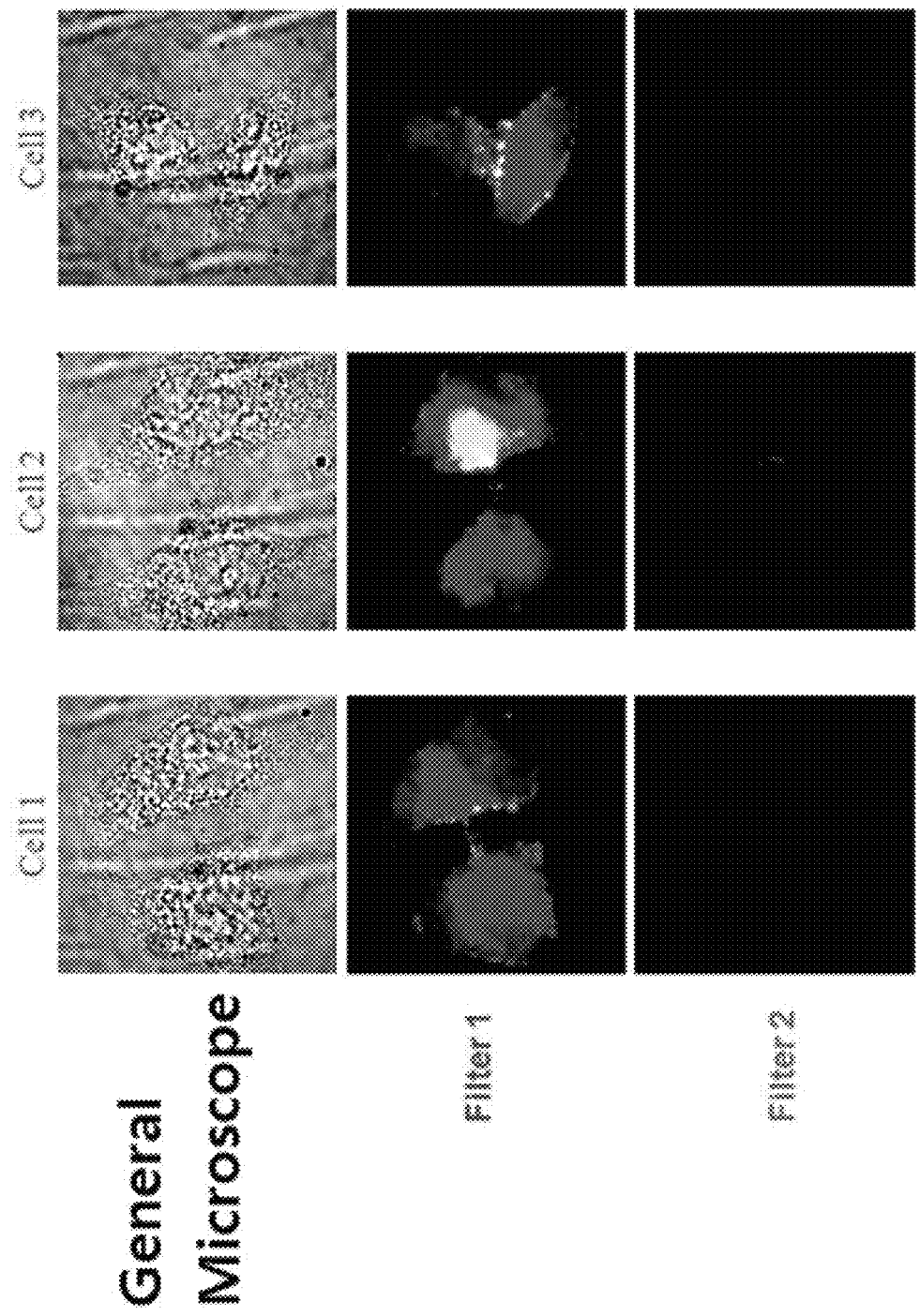
FIG. 11 shows cell images of three sections of the test group incubated with the PEG-coated nanoparticles of Synthesis Example 4, as measured by the apparatus of the present invention using two narrow band pass filters ("Filter 1" and "Filter 2").

FIG. 11 shows cell images of three sections of the test group incubated with the PEG-coated nanoparticles of Synthesis Example 4, as measured by the apparatus of the present invention using two narrow band pass filters ("Filter 1" and "Filter 2").

Figure 12:
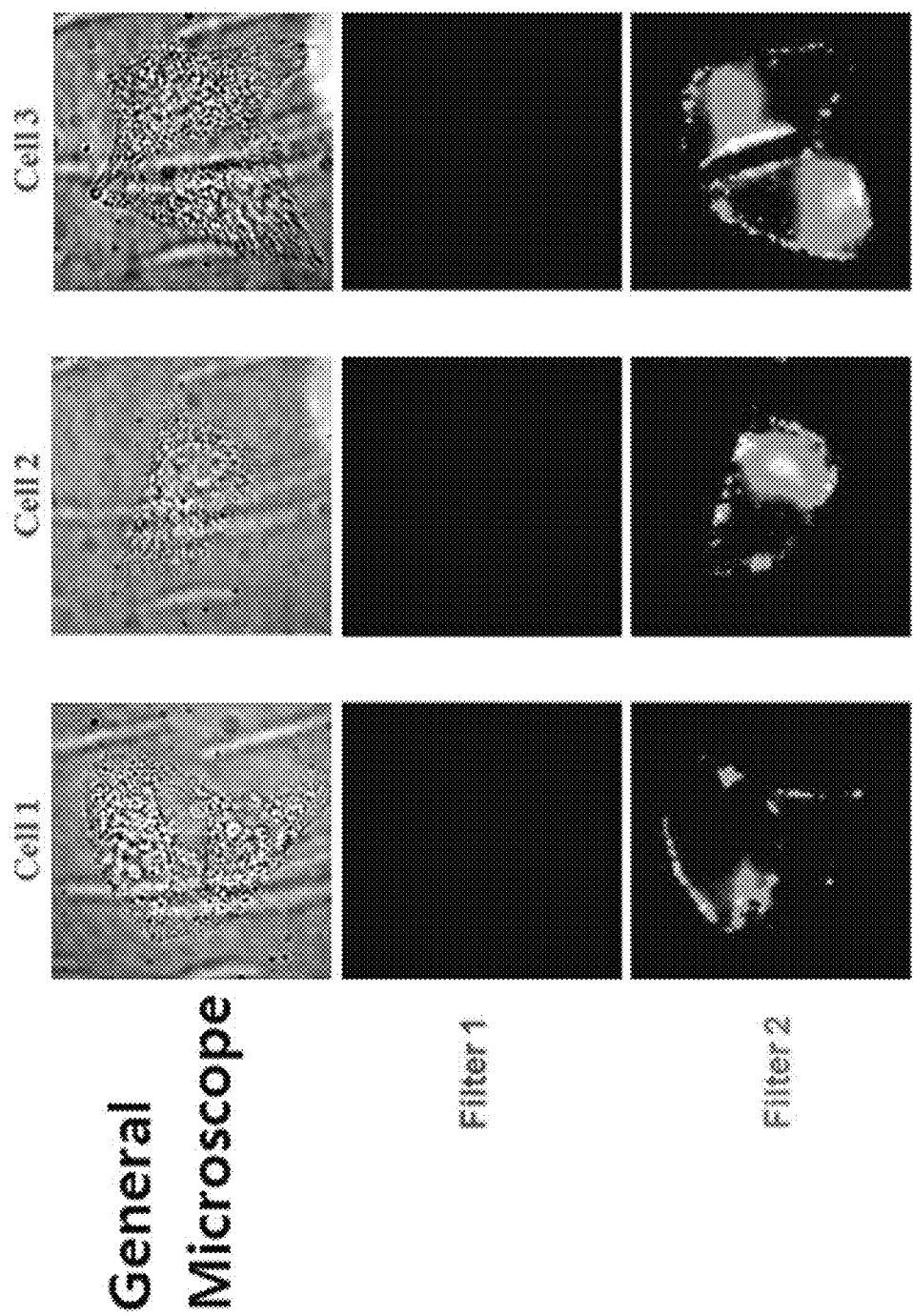
FIG. 12 shows cell images of three sections of the test group incubated with the PEG-coated nanoparticles of Synthesis Example 5, as measured by the apparatus of the present invention using two narrow band pass filters ("Filter 1" and "Filter 2").

FIG. 12 shows cell images of three sections of the test group incubated with the PEG-coated nanoparticles of Synthesis Example 5, as measured by the apparatus of the present invention using two narrow band pass filters ("Filter 1" and "Filter 2").

As can be seen in FIGS. 10 to 12, Raman images of cells were obtained only through "Filter 2" because it selectively transmitted the signals of the PEG-coated nanoparticles synthesized in Synthesis Example 5. It is understood that these images were not attributed to the autofluorescence of cells, but to Raman signals scattered from the PEG-coated nanoparticles associated with the cells.

<Description of the Reference Numerals in the Drawings>

| | |
|---|---|
| 10: Light Source | 20: Spatial Filter |
| 21: Beam Splitter | 30: Objective Lens |
| 40: Raman Filter | 50: Motion Controller |
| 60: Mirror | 110: Computer |
| 111: Detector (CCD camera) | |

The invention claimed is:

1. A high-speed screening apparatus of multiple drugs using surface-enhanced Raman scattering, comprising:
    an excitation module, composed of a lens, a mirror, and a pinhole, for introducing a light beam from a light source into a microscope;
    a microscope module for acquiring an image of a sample to be analyzed, wherein the sample contains a core-gap-shell nanoparticle, comprising:
        a motion controller for controlling a position of a well plate,
        a filtration unit composed of one or more Raman filters for filtering Raman wavelengths against light scattered from the sample when the sample is irradiated with excitation light from the light source, and
        a CCD (charge-coupled device) camera operating in a non-scanning manner for sequentially receiving light beams passing through the filtration unit; and
    an image processing module for coding colors for a set of images obtained from a point containing a sample to produce cell or tissue images, and for displaying the cell or tissue images, said point being positioned by the motion controller,
    wherein the CCD camera takes Raman images of the sample from an individual well of the well plate at once in a non-scanning manner and the wells are sequentially brought into a photographing site by the motion controller well by well; and
    wherein the core-gap-shell nanoparticle comprises a core consisting of a metal exhibiting surface plasmon resonance; a shell consisting of a metal exhibiting surface plasmon resonance surrounding the core; and a nanogap formed therebetween, said core having a first portion and a second portion, wherein the first portion of said core is connected with the shell via a nanobridge and the second portion of said core is not connected with the shell via a nanobridge, said nanogap containing an optically Raman active molecule consisting of an atom selected from the group consisting of C, H, O, N, S, and a combination thereof therein.

2. The high-speed screening apparatus of claim 1, further comprising an XY translational stage connected to the motion controller.

3. The high-speed screening apparatus of claim 1, wherein the light source emits light at a wavelength between from 400 to 700 nm.

4. The high-speed screening apparatus of claim 1, wherein the filtration unit is composed of 1 to 20 Raman filters.

5. The high-speed screening apparatus of claim 1, wherein the set of images is composed of 1 to 20 images.

6. The high-speed screening apparatus of claim 1, wherein the sample is a cell.

7. The high-speed screening apparatus of claim 6, wherein the cell is selectively associated with a core-gap-shell nanoparticle for Raman imaging.

8. A high-speed screening method of multiple drugs using the apparatus of claim 1, comprising:
adding core-gap-shell nanoparticles to a sample to be analyzed (step 1);
obtaining one or more Raman images from the sample by irradiating a laser beam on the sample to generate Raman scattered light, filtering the Raman scattered light through a filtration unit composed of one or more Raman filters to extract a Raman wavelength of interest, and detecting the Raman spectrum using a CCD (charge-coupled device) camera operating in a non-scanning manner (step 2); and
coding colors for the Raman images of the sample to generate cell or tissue images and displaying the cell or tissue images (step 3),
wherein the laser beam has a diameter which can take Raman images in a non-scanning manner from individual well of well plate,
wherein the CCD camera takes one or more Raman images of the sample in the individual well of the well plate as the wells are sequentially brought into a photographing site by the motion controller, and
wherein the core-gap-shell nanoparticle comprises a core and a shell surrounding the core, with a nanogap formed therebetween, said core having a first portion and a second portion, wherein the first portion of said core is connected with the shell via a nanobridge and the second portion of said core is not connected with the shell via a nanobridge, said nanogap containing an optically active molecule therein, and
the core consists of a metal exhibiting surface plasmon resonance, and the shell consists of a metal exhibiting surface plasmon resonance, and
the optically active molecule is a molecule consisting of an atom selected from the group consisting of C, H, O, N, S, and a combination thereof.

9. The high-speed screening method of claim 8, wherein the filtration unit is composed of 1 to 20 Raman filters.

10. The high-speed screening method of claim 8, wherein the step 3 is carried out by coding 1 to 20 colors for the Raman images of the sample obtained in step 2 using a computer program to give color-coded Raman images and displaying the color-coded Raman images ranging in multiplexity from 1 to 20.

11. A high-speed screening method of multiple drugs using the apparatus of claim 1, comprising:
adding core-gap-shell nanoparticles to a sample to be analyzed (step 1);
obtaining one or more Raman images from the sample by irradiating a laser beam on the sample to generate Raman scattered light, filtering the Raman scattered light through a filtration unit composed of one or more Raman filters to extract a Raman wavelength of interest, and detecting the Raman spectrum using a CCD (charge-coupled device) camera operating in a non-scanning manner (step 2); and
coding colors for the Raman images of the sample to generate cell or tissue images and displaying the cell or tissue images (step 3),
wherein the laser beam has a diameter of about 10 mm,
wherein the CCD camera takes one or more Raman images of the sample in the individual well of the well plate as the wells are sequentially brought into a photographing site by the motion controller, and
wherein the core-gap-shell nanoparticle comprises a core and a shell surrounding the core, with a nanogap formed therebetween, said core having a first portion and a second portion, wherein the first portion of said core is connected with the shell via a nanobridge and the second portion of said core is not connected with the shell via a nanobridge, said nanogap containing an optically active molecule therein, and
the core consist of a metal exhibiting surface plasmon resonance, and the shell consist of a metal exhibiting surface plasmon resonance, and
the optically active molecule is a molecule consisting of an atom selected from the group consisting of C, H, O, N, S, and a combination thereof.

12. A high-speed screening apparatus of multiple drugs using surface-enhanced Raman scattering, comprising:
a well plate comprising a plurality of wells, wherein at least one of said plurality of wells contains a cell as a sample to be analyzed and a core-gap-shell nanoparticle;
an excitation module, composed of a lens, a mirror, and a pinhole, for introducing a light beam from a light source into a microscope;
a microscope module for acquiring an image of a sample, comprising:
a motion controller for controlling a position of the well plate (well to well),
a filtration unit composed of one or more Raman filters for filtering Raman wavelengths against light scattered from the sample when the sample is irradiated with excitation light from the light source, and
a CCD (charge-coupled device) camera operating in a non-scanning manner for sequentially receiving light beams passing through the filtration unit;
an image processing module for coding colors for a set of images obtained from a point containing a sample to produce cell or tissue images, and for displaying the cell or tissue images, said point being positioned by the motion controller,
wherein the CCD camera takes Raman images of the sample for the individual well of the well plate at once in a non-scanning manner and the wells are sequentially brought into a photographing site by the motion controller well by well; and
wherein the core-gap-shell nanoparticle comprises a core consisting of a metal exhibiting surface plasmon resonance; a shell consisting of a metal exhibiting surface plasmon resonance surrounding the core; and a nanogap formed therebetween, said core having a first portion and a second portion, wherein the first portion of said core is connected with the shell via a nanobridge and the second portion of said core is not connected with the shell via a nanobridge, said nanogap containing an optically active molecule consisting of an atom selected from the group consisting of C, H, O, N, S, and a combination thereof therein.

* * * * *